United States Patent

Kohrs

[11] Patent Number: 5,478,342
[45] Date of Patent: Dec. 26, 1995

[54] REVERSIBLE BONE SCREW LOCK

[75] Inventor: Douglas W. Kohrs, Edina, Minn.

[73] Assignee: Spinetech, Inc., Minneapolis, Minn.

[21] Appl. No.: 268,281

[22] Filed: Jun. 30, 1994

[51] Int. Cl.$^6$ .................................................. A61B 17/86
[52] U.S. Cl. .................................................. 606/73
[58] Field of Search .................... 606/73, 72, 65, 606/66, 67, 68; 411/140, 395, 379, 383, 386, 21, 359

[56] References Cited

U.S. PATENT DOCUMENTS

| | | |
|---|---|---|
| 231,588 | 8/1880 | Kernochan . |
| 324,768 | 8/1885 | Hunt . |
| 867,429 | 10/1907 | Simmerman . |
| 1,075,911 | 8/1913 | Gobin . |
| 2,631,584 | 3/1953 | Purificato . |
| 2,998,007 | 8/1961 | Herzog . |
| 3,204,785 | 3/1962 | Dobelle . |
| 3,579,831 | 5/1971 | Stevens et al. . |
| 3,618,212 | 11/1971 | Weissman . |
| 4,190,044 | 2/1980 | Wood . |
| 4,636,121 | 1/1987 | Miller ........................ 411/140 |
| 5,087,260 | 2/1992 | Fixel . |
| 5,338,197 | 8/1994 | Kwan . |

FOREIGN PATENT DOCUMENTS

| | | | |
|---|---|---|---|
| 2845000 | 4/1980 | Germany ........................ 411/21 |
| 3738233 | 5/1989 | Germany ........................ 411/21 |
| 200478 | 12/1965 | Sweden ........................ 606/68 |

Primary Examiner—Tamara L. Graysay
Attorney, Agent, or Firm—Vidas, Arrett & Steinkraus

[57] ABSTRACT

A medical bone screw including a lock to lessen the possibility of pull-out or screw-out. The screw may be any bone screw including a cannula. A wire spring is inserted partially into the cannula prior to use. Once in position, the wire spring is pushed further down the cannula until its ends may project out side openings in the screw. These projections lock the screw in place. Further depression of the wire spring disengages them so the screw may be removed.

2 Claims, 4 Drawing Sheets

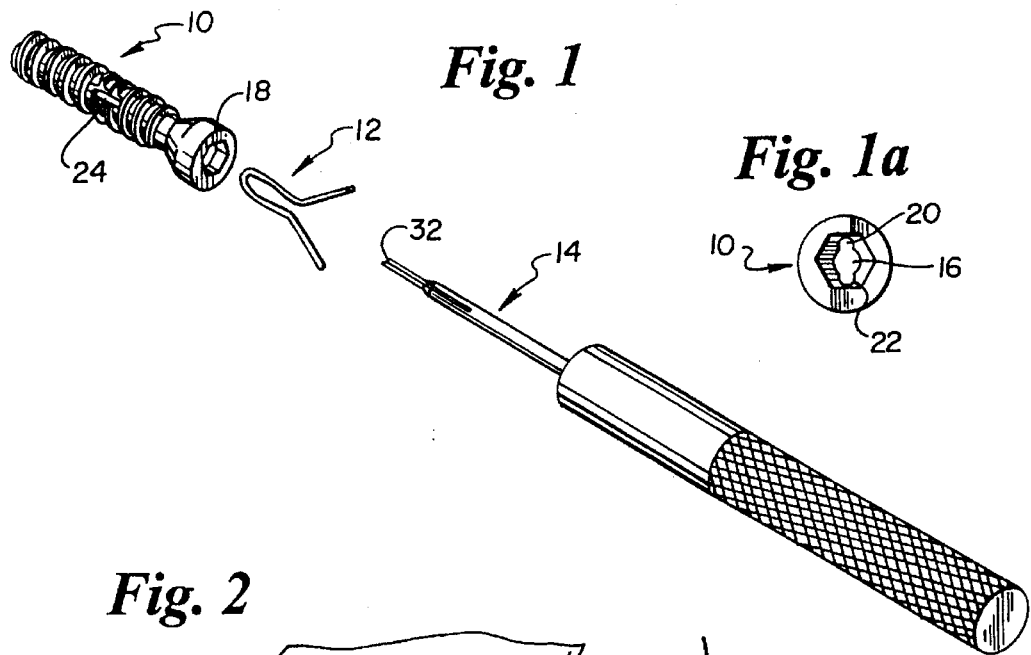
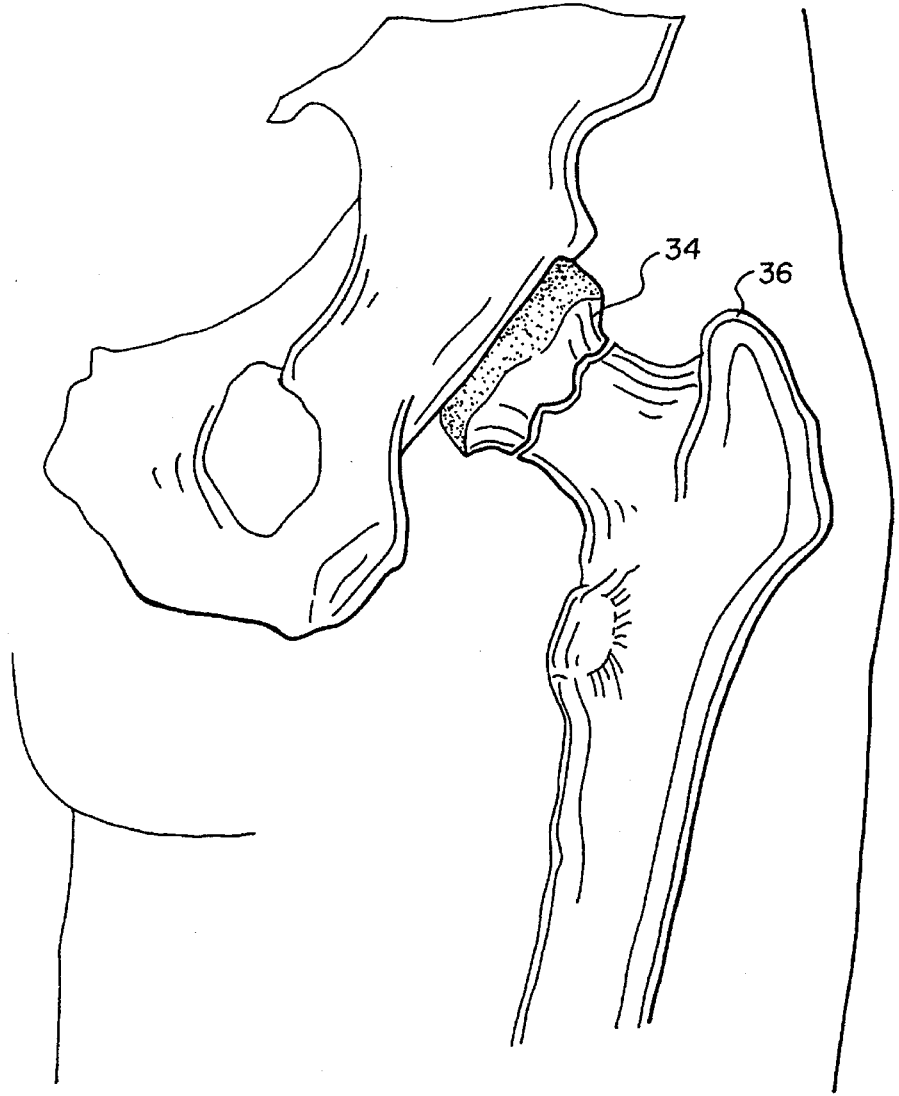

5,478,342

REVERSIBLE BONE SCREW LOCK

BACKGROUND OF THE INVENTION

1. Field of the Invention

This invention relates to a locking bone screw that is reversible.

2. Description of the Related Art

Bone screws are used in a great variety of applications to fix bones, bone fragments, or to act as an anchor for bone plates, rods, etc. In some applications, it is critical to prevent the screws from backing out, since their position may be near vessels, nerves or other implant components which could be damaged.

Many attempts have been made to create a usable locking bone screw. Most are quite complicated and are not readily removable when desired. Positive locking of bone screws is very desirable, since in some applications, even minor pull-out or screw-out could cause contact with a vital structure in the body. Even of greater need is a positively locking bone screw which could be removed if desired.

The art described in this section is not intended to constitute an admission that any patent, publication or other information referred to herein is "prior art" with respect to this invention, unless specifically designated as such. In addition, this section should not be construed to mean that a search has been made or that no other pertinent information as defined in 37 C.F.R. §1.56(a) exists.

SUMMARY OF THE INVENTION

The present invention provides a simple cannulated bone screw that includes at least one side opening. A spring is inserted into the cannula while a prong is able to spring out of a side opening into the surrounding bone. The presence of the spring ends in the bone makes screw-out very unlikely since the spring ends must carve out its own threads.

It is possible to remove or reposition bone screws of this invention. One simply needs to depress the spring further down the cannula to disengage the spring ends. The screw may then be removed and repositioned.

One or more spring ends and matching side openings may be employed. The cannula may include guides to make alignment of the spring ends with the side holes easier. Generally, any bone screw design may be used which may be cannulated and made with side openings.

BRIEF DESCRIPTION OF THE DRAWINGS

A detailed description of the invention is hereafter described with specific reference being made to the drawings in which:

FIG. 1 is a perspective view of a bone screw, lock spring;

FIG. 1a is an end view of the screw showing the cannula and guides;

FIG. 2 shows a typical bone break in need of repair;

DESCRIPTION OF THE PREFERRED EMBODIMENTS

Figure 3:
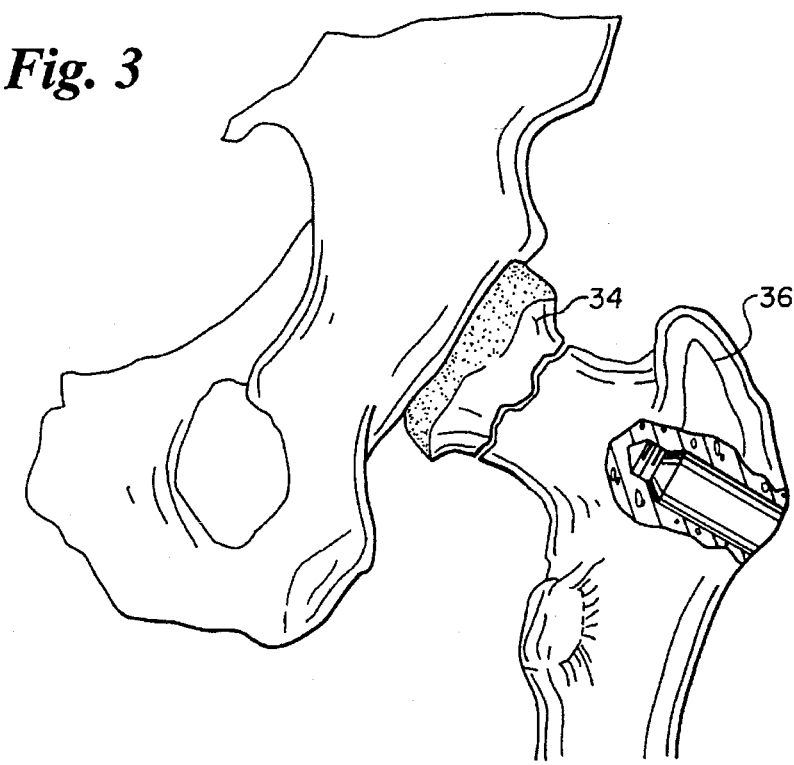
FIG. 3 shows the bone of FIG. 2 being prepared for a screw.
Figure 4:
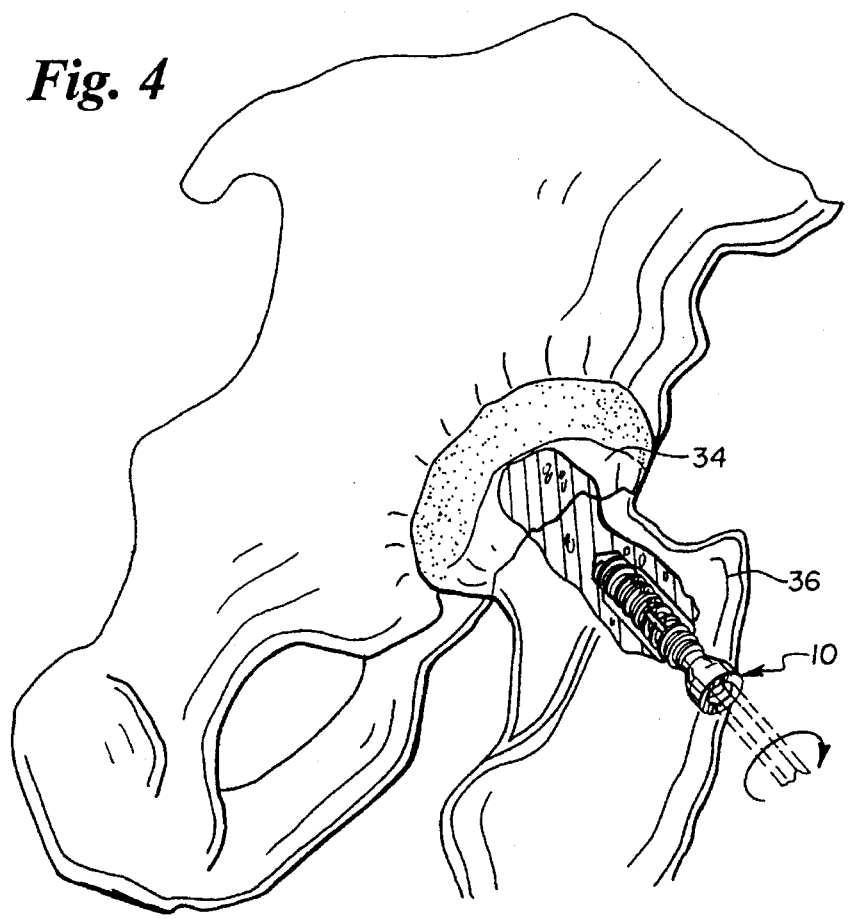
FIG. 4 shows insertion of the bone screw typically with an allen wrench.

With reference to the figures, FIG. 1 shows a bone screw 10, spring 12, and inserting tool 14 of the invention. As seen in FIG. 1a, bone screws 10 include a cannula 16 and a head 18 which accepts an allen wrench driver. The shaft 11 of the screw 10 is threaded as shown. The cannula 16 is preferably formed with spring guides 20, 22 which makes it easier to insert the spring and to align the spring 12 in the cannula. The cannula 16 preferably extends throughout the length of the screw to allow a spring 12 to pass from one end and out the other. The cannula 16 may extend only from the head partially down the length of the screw 10.

Intermediate the ends of the bone screw 10 are a pair of opposing side openings 24, 26 which communicate with the cannula 16. The spring 12 as shown in FIGS. 1, 5, 6, 6a has two ends 28, 30 (See FIG. 5) which are positioned in spring guides 20, 22 of the cannula 16. An insertion tool 14 with a U-shaped end 32 is pushed into the cannula, engaging the spring 12 and depressing it further into the cannula 16.

Figure 5:
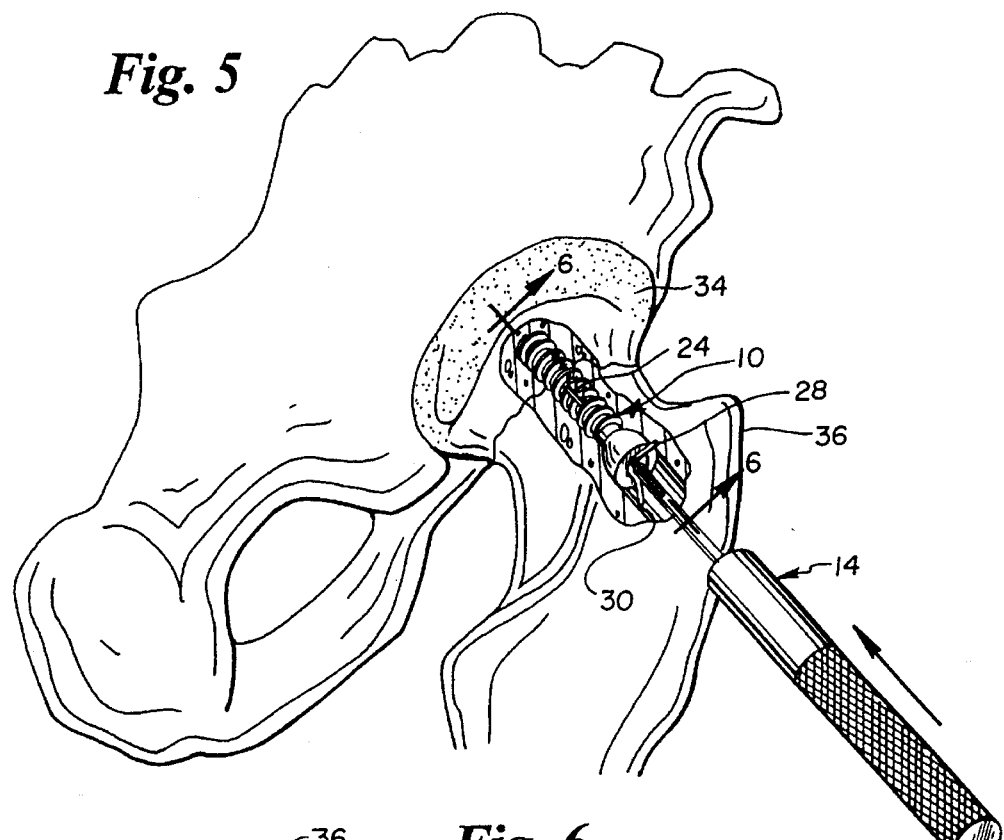
FIG. 5 shows insertion of a spring into the cannula after the bone screw is fully seated.
Figure 6:
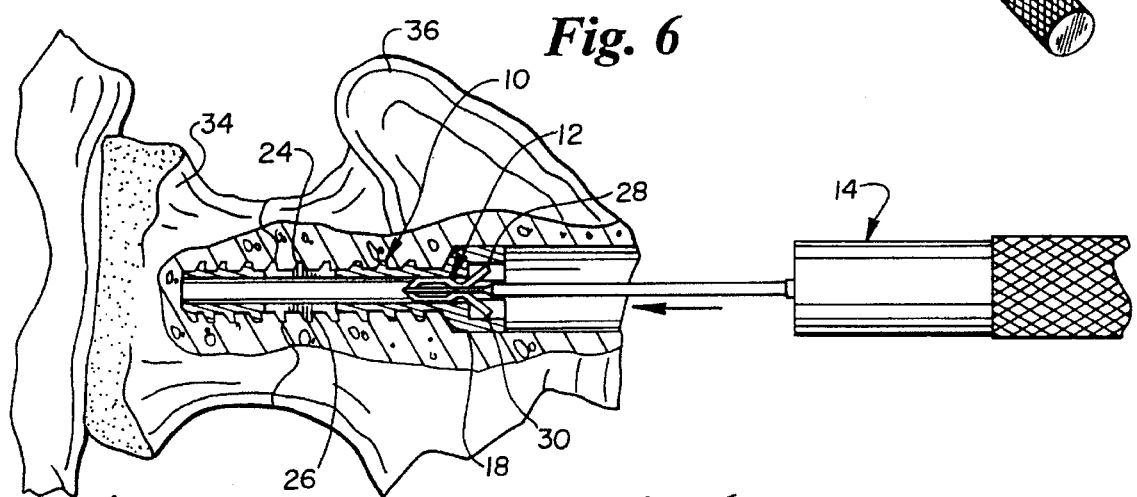
FIG. 6 is a cross-section view of lines 6.6 of FIG. 5 showing the spring insertion.
Figure 7:
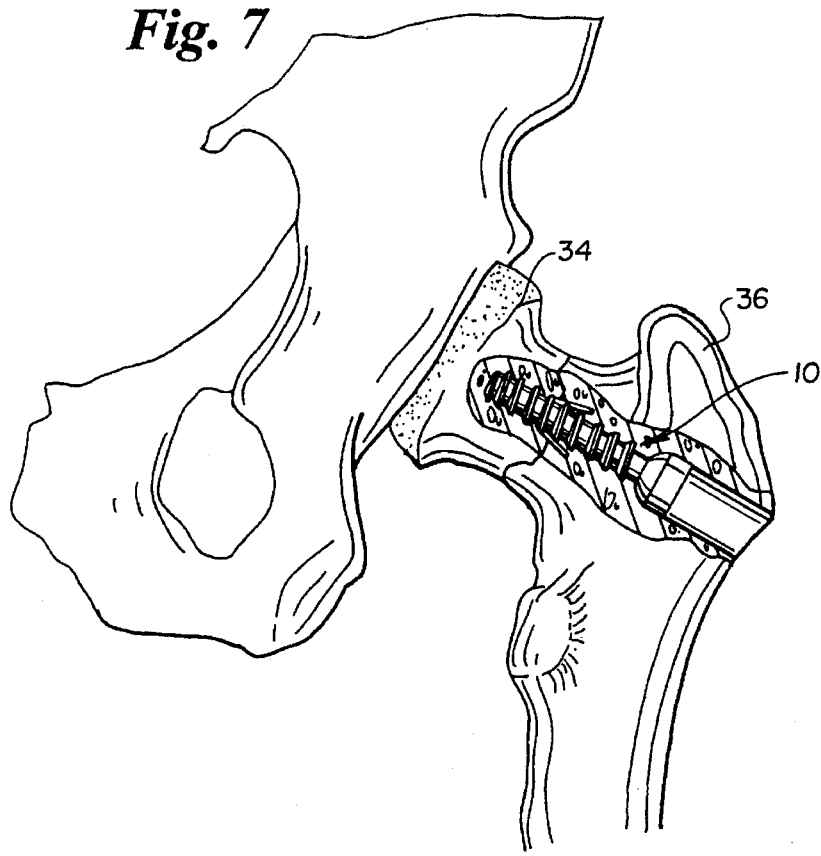
FIG. 7 shows a variant having four spring ends and side openings.

With reference to FIGS. 2–7, it will be seen that a bone fracture of bone segments 34, 36 may be readily joined with the invention. As shown in FIG. 3, an opening 50 is formed in the bone which may be countersunk 52 as shown. The bone screw 10, preferably with spring 12 pre-inserted (in the springs' compressed stage), is threaded into the bone with an allen wrench or similar device to torque the screw into place as shown in FIGS. 5–7.

Figure 6A:
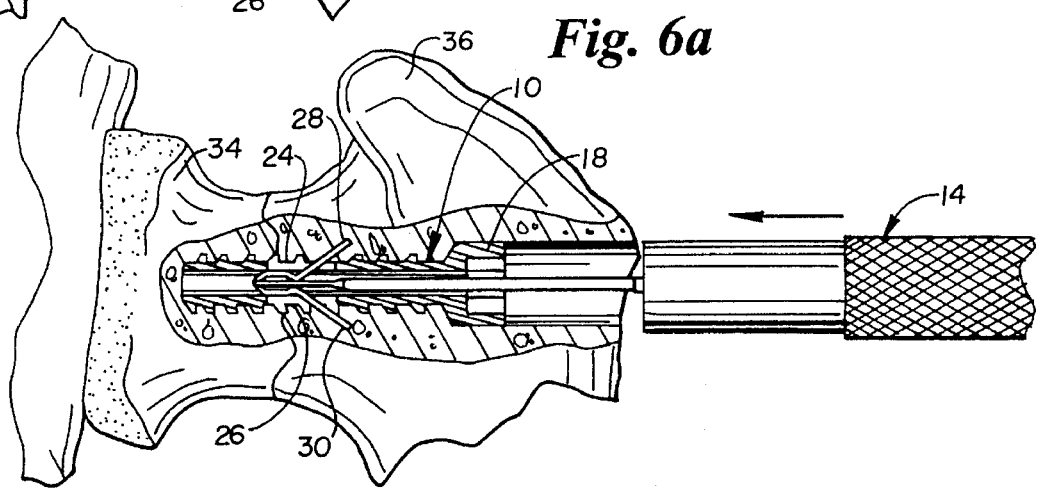
FIG. 6a is a view similar to FIG. 6 showing the spring ends projecting through side holes.

Once the bone screw 10 is at the desired depth, the inserting tool, or any device that can contact the spring 12 and depress it down the cannula 16 is employed. The inserting tool 14 as shown has a u-shaped end 32 that catches the spring 12 readily. The spring 12 is depressed down the cannula 16 until the spring ends 28, 30 are able to pass out through the side openings 24, 26 as shown in FIG. 6a. The spring 12 is constructed such that the ends 28, 30 will be forced outwardly into the bone and will actually extend into the bone further than the tapped threads. This helps to lock the bone screw 10 in place, since the spring ends 28, 30 would need to tear out through bone or twist out to form an enlarged thread or groove to loosen.

Figure 8:
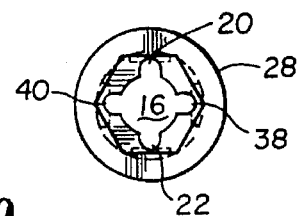
FIG. 8 is an end view of the bone of FIG. 7 showing multiple cannula spring guides.
Figure 9:
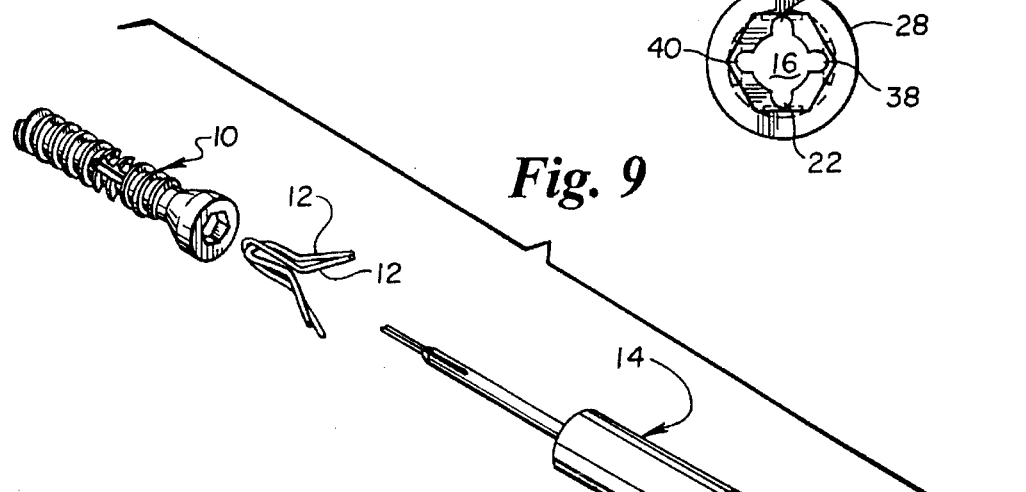
FIG. 9 is a perspective view showing a bone screw lock with the four pronged spring to be positioned.

FIGS. 7–9 show that the bone screws 10 of the invention may have multiple springs 12, spring guides 38, 40 in addition to guides 20, 22; and additional side openings. The spring 12 may be formed as a single unit with four projecting ends, each of which would pass through a matching side opening. It should be apparent that a single spring end up to many spring ends may be employed.

Figure 10:
FIG. 10 is a perspective view showing two 4-pronged bone screws to be positioned.

FIG. 10 shows a bone screw 10 having two separate side openings 44, 46 that are spaced apart along the shaft. In this form, a spring 12 may be inserted until the spring ends 28 project through opening 44 to lock into bone. If the depth of the screw must be readjusted, but not removed, the spring is simply depressed down the shaft to disengage the lock. The screw could then be positioned deeper and the spring would be advanced down to opening 46 to relock. This also makes it easy to reuse the screw if it needs to be removed for repositioning.

If the bone screw needs to be removed for any reason, other locking bone screws are nearly impossible to remove. With the device of the invention, one simply depresses the spring 12 further down the cannula 16 so the spring ends 28, 30 re-enter the cannula and are held fully inside the device.

The bone screw and spring may be formed from any biocompatible material such as is well known in the art. Stainless steels, titanium and nitinol alloys are examples for both the screw body and the spring. The spring may be formed to provide more or less outward spring force.

Any bone screw that may be cannulated may be modified to benefit from this invention. Primarily, bone screws intended for use in cancellous bone may use this invention.

While this invention may be embodied in many different forms, there are shown in the drawings and described in detail herein specific preferred embodiments of the invention. Procedures that may employ the inventive devices include bone plate fixation generally, pedicle screw use, tibial tray fixation, cervical plate fixation, total hip acetabular cup fixation and intramedullary rod fixation. The present disclosure is an exemplification of the principles of the invention and is not intended to limit the invention to the particular embodiments illustrated.

This completes the description of the preferred and alternate embodiments of the invention. Those skilled in the art may recognize other equivalents to the specific embodiment described herein which equivalents are intended to be encompassed by the claims attached hereto.

What is claimed is:

1. A reversible locking bone screw comprising:

(a) a threaded shaft including a head at a proximal end for turning said screw, said screw including a cannula extending distally from said head into said threaded shaft;

(b) a pair of opposing side openings formed through said threaded shaft to communicate with said cannula;

(c) a spring wire shaped to define a vee having two spring ends normally spring-biased away from each other, each spring end of which may extend through said side openings;

(d) said cannula including opposing spring guide grooves extending from said head to said side openings for guiding said spring ends to said side openings, said cannula extending from said head distally of said side openings such that said spring wire may be inserted past said side openings such that said spring wire ends may re-enter the cannula distally of the side openings.

2. The reversible locking bone screw of claim 1 wherein said shaft includes a second pair of side openings spaced directly distally of said first side openings.

* * * * *